United States Patent [19]

Gupta

[11] Patent Number: 4,851,000

[45] Date of Patent: Jul. 25, 1989

[54] BIOPROSTHETIC VALVE STENT

[75] Inventor: Brij M. Gupta, Mission Viejo, Calif.

[73] Assignee: Pacific Biomedical Holdings, Ltd., Singapore

[21] Appl. No.: 80,313

[22] Filed: Jul. 31, 1987

[51] Int. Cl.[4] .............................................. A61F 2/24
[52] U.S. Cl. ...................................................... 623/2
[58] Field of Search ........................................... 623/2

[56] References Cited

U.S. PATENT DOCUMENTS

| | | |
|---|---|---|
| Re. 30,912 | 4/1982 | Hancock . |
| 3,197,788 | 8/1965 | Segger . |
| 3,320,972 | 4/1964 | High et al. . |
| 3,445,916 | 5/1969 | Schulte . |
| 3,548,418 | 12/1970 | Angell et al. . |
| 3,570,014 | 9/1968 | Hancock . |
| 3,608,097 | 9/1971 | Bellhouse et al. . |
| 3,714,671 | 2/1973 | Edwards et al. . |
| 3,736,598 | 6/1973 | Bellhouse et al. . |
| 3,739,402 | 6/1973 | Cooley et al. . |
| 3,744,060 | 7/1973 | Bellhouse et al. . |
| 3,744,062 | 7/1973 | Parsonnet . |
| 3,755,823 | 9/1973 | Hancock . |
| 3,983,581 | 10/1976 | Angell et al. . |
| 4,035,849 | 7/1977 | Angell et al. . |
| 4,079,468 | 3/1978 | Liotta et al. . |
| 4,084,268 | 4/1978 | Ionescu et al. . |
| 4,106,129 | 8/1978 | Carpentier et al. . |
| 4,172,295 | 10/1979 | Batten . |
| 4,192,020 | 3/1980 | Davis et al. . |
| 4,222,126 | 9/1980 | Boretos et al. . |
| 4,247,292 | 1/1981 | Angell . |
| 4,259,753 | 4/1981 | Liotta et al. . |
| 4,265,694 | 5/1981 | Boretos et al. . |
| 4,291,420 | 9/1981 | Reul . |
| 4,340,977 | 7/1982 | Brownlee et al. . |
| 4,343,048 | 8/1982 | Ross et al. . |
| 4,345,340 | 8/1982 | Rosen . |
| 4,364,126 | 12/1982 | Rosen et al. . |
| 4,364,127 | 12/1982 | Pierce et al. . |
| 4,372,743 | 2/1983 | Lane . |
| 4,441,216 | 4/1984 | Ionescu et al. . |
| 4,443,895 | 4/1984 | Lane . |
| 4,451,936 | 6/1984 | Carpenter et al. . |
| 4,470,157 | 9/1984 | Love . |
| 4,477,930 | 10/1984 | Totten et al. . |
| 4,490,859 | 1/1985 | Black et al. . |
| 4,501,030 | 2/1985 | Lane . |
| 4,506,394 | 3/1985 | Bedard . |
| 4,581,028 | 4/1986 | Fox, Jr. et al. . |
| 4,605,407 | 8/1986 | Black et al. . |
| 4,610,688 | 9/1986 | Silvestrini et al. . |

Primary Examiner—V. Millin
Assistant Examiner—James Prizant
Attorney, Agent, or Firm—Pravel, Gambrell, Hewitt, Kimball & Krieger

[57] ABSTRACT

The stent structure of the present invention would utilize an annular base ring defining an inflow orifice, with at least two circumferentially-spaced posts molded into the annular base ring at one end, and at their upper ends, molded into an upper ring comprising at least bi-segmented parabolic shaped scallops. The posts, which are constructed of spring steel molded in place, would provide the flextral capability necessary to allow relative movement between the scallops of the upper ring and the annular base. The parabolic-shaped segments taken together form a right cylinder of the inside diameter of the valve. The parabolic shape of the scallops reduce stress on the valve cusps.

7 Claims, 2 Drawing Sheets

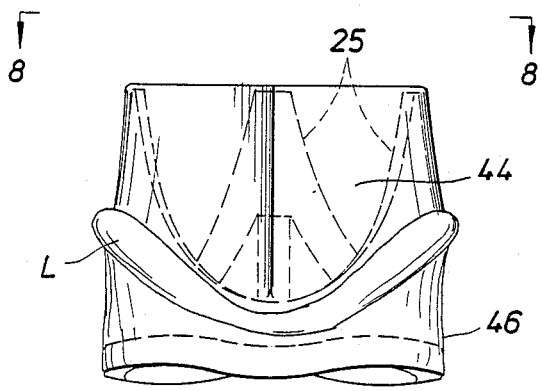
FIG. 7
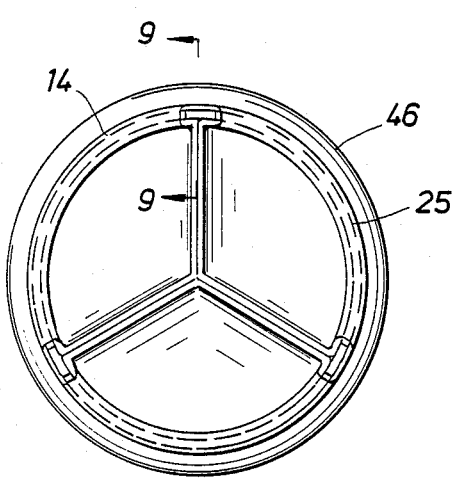
FIG. 8
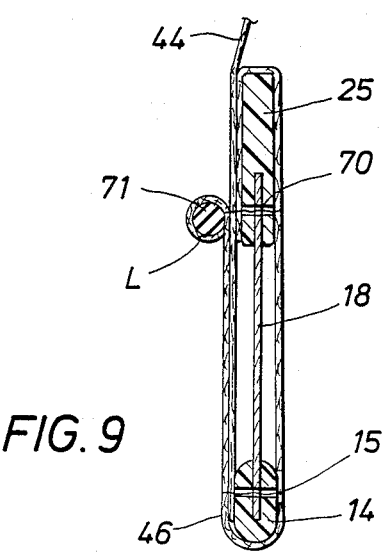
FIG. 9
FIG. 10
FIG. 11
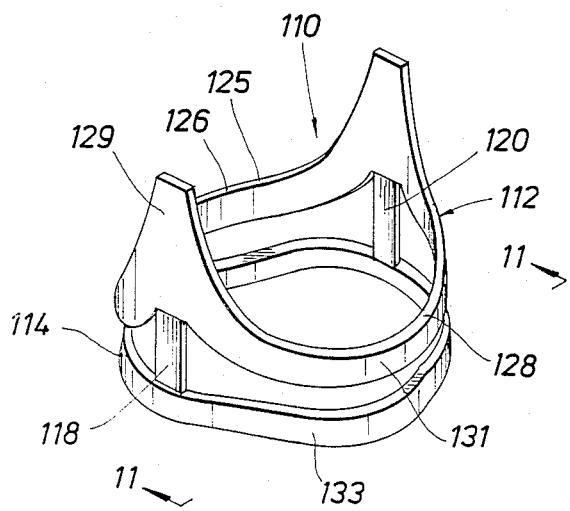
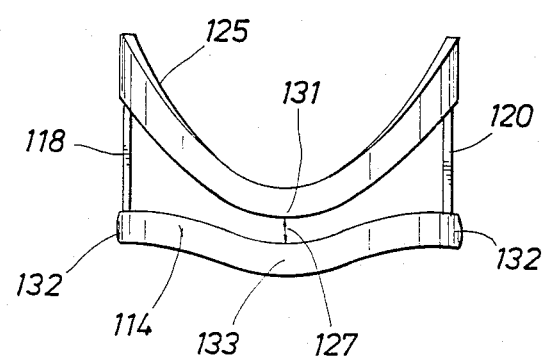

BIOPROSTHETIC VALVE STENT

BACKGROUND OF THE INVENTION

1. Field Of The Invention

The present invention relates to bioprosthetic valves. More particularly, the present invention relates to a valve stent, including an upper ring formed of multi-segmented parabolic-shaped scalloped rings, the valve stent formed of a polymer and spring steel composite structure.

2. General Background

Valve prostheses have been utilized in surgical applications to replace various diseased or damaged natural valves, more particularly, heart valves including the aortic valve, the mitral valve and the tricuspid valve. In general, the failure of tissue heart valves have primarily been attributed to calcification and premature degeneration of tissue used to fabricate the valve. Although reasons for calcification of the tissue in these devices are still not well understood it is believed that excessive mechanical stresses are experienced by the tissue during their opening and closing function.

For example, in U.S. Pat. No. 4,343,048 issued to Ross, et al, entitled "Stent For A Cardiac Valve," the patented stent includes a metal base ring having metal legs projecting therefrom in a generally axial direction so that each of the legs can be resiliently deformed over substantially its whole axial length to take up strain in the valve without impairing its performance. The patent stresses that the base ring of the stent would be substantially rigid so that as pressure conditions occur within the heart, the base ring would not deform to any substantial extent. In addition, each leg would be shaped so that as it would project from the base ring, it would curve inwardly toward the axis of the stent in a "fishing rod structure" to avoid excessive stresses on the valve.

In recognizing problems in the present state of the art, an attempt to avoid valve failure has been the incorporation of a flexible polymer stent or valve frame. However, even with the use of the polymer stents, permanent deformation of these frames or stents due to polymer creep often results in failure of tissue valves using plastic frames.

As will be appreciated from the following description, it is possible in accordance with the present invention to provide a method to achieve complete flexibility of the valve frame without resulting polymer creep. A composite structure of polymer and spring steel is incorporated into the valve frame. Metal inserts of spring steel are injection molded into place at 120° apart to form three vertical posts of the frame in the case of a tricuspid valve or 180° apart to form two vertical posts in the case of a bicuspid valve. The flex life of this spring steel under worse conditions of physiological pressures would theoretically be infinite.

The frame would include an annular base ring defining an inflow orifice of the valve. If the valve is intended for use in the heart, this base ring is designed to proximate the physiological shape of the aortic valve annulus. If the valve is intended for use in a vein, the base ring is designed to proximate the physiological shape of the inner annular wall of the vein or vessel. In the preferred embodiment, there are molded into this ring three equally spaced frame posts joined by an upper ring comprising tri-segmented parabolic-shaped scallops. The upper scalloped ring defines generally three parabolic shaped one-third portions of the base between the center lines of the respective posts which together form a right cylinder of inside diameter of the valve. In the alternate embodiment, two oppositely spaced frame posts are molded into the base ring. The top of each frame post is joined by an upper ring comprising bi-segmented parabolic-shaped scallops. The parabolic shape of the scallops of the upper rings will reduce stress on the valve cusps. Cusp failure of existing tissue valves have been related generally to the ellipsoid shape of scalloping rings.

The scallops of the upper ring of the valve remain free and independent of the implant annulus to allow complete flexibility of the posts and the scallops. In the existing parabolic devices, the scallops form a part of the sewing ring which is tied down to the valve annulus during valve implantation thereby rendering the scalloping rings inflexible. This in turn would restrict the flex of the frame posts and expose valve cusps to higher stresses. In the present invention, the suture ring of the valve, which is constructed between the lower ring and the scallops of the upper ring, remains away and detached from cusp tissue.

The frame assembly may then be covered with fabric. Although this is not an essential feature, there are certain advantages to a fabric covered valve frame.

SUMMARY OF THE PRESENT INVENTION

The bioprosthetic valve stent structure of the present invention would utilize an annular base ring defining the inflow orifice. In the preferred embodiment, three circumferentially-spaced posts are molded into the annular base ring at one end. At their upper ends is molded an upper ring comprising tri-segmented parabolic shaped scallops. The alternate embodiment is composed of two oppositely spaced frame posts also molded at one end to the annular base and at their upper end to an upper ring comprising bi-segmented parabolic-shaped scallops. The posts, which are constructed of spring steel molded in place, would provide the flextral capability necessary to allow relative movement between the scallops of the upper ring and the annular base ring. The parabolic-shaped segments taken togther form a right cylinder of the inside diameter of the valve. The parabolic shape of the scallops reduce stress on the valve cusps. A suture ring would then be constructed between the annular ring and the scalloped upper ring.

BRIEF DESCRIPTION OF THE DRAWINGS

In order that the invention may be more fully understood, embodiments in accorance therewith will now be described with reference to the accompanying drawings, wherein:

FIGS. 7 and 8 illustrate overall side and top views respectively of the preferred embodiment of the stent, following attachment of a tricuspid valve body and skirt portion;

FIG. 9 is a cross-sectional view along line 9—9 in FIG. 8;

FIG. 10 represents an overall perspective view of an alternate embodiment of the present invention; and FIG. 11 is a side elevation view of the alternate embodiment shown in FIG. 10.

DETAILED DESCRIPTION OF THE INVENTION

Figure 1:
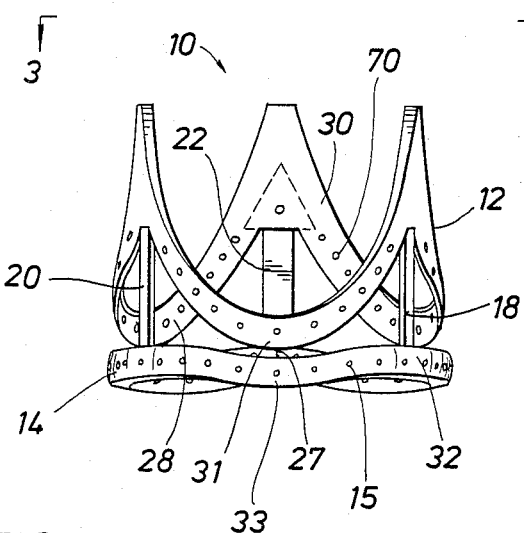
FIG. 1 represents a front elevation view of the preferred embodiment of the present invention illustrating the parabolic shape of the upper ring of the valve stent.
Figure 2:
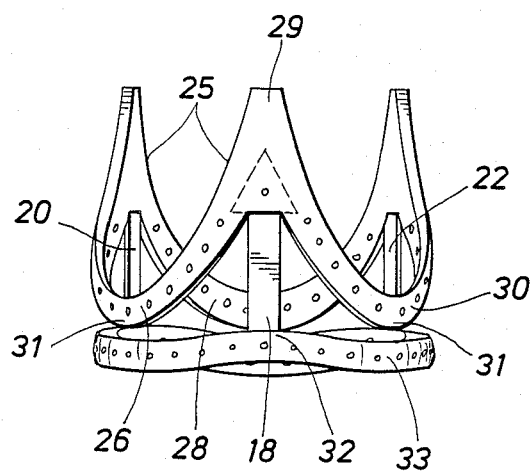
FIG. 2 is a side elevation view of the assembly of FIG. 1, illustrating in full view one of the posts in the valve stent.
Figure 3:
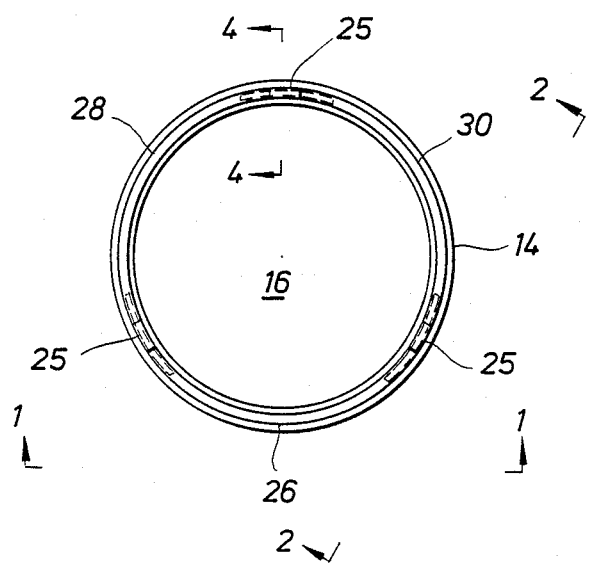
FIG. 3 is an overall top view of the preferred embodiment of the valve stent of the present invention.

FIGS. 1-9 illustrate the preferred embodiment of the biprosthetic valve stent of the present invention by the numeral 10. As seen in FIGS. 1-9, more particularly FIGS. 1 and 2, valve stent 10 would comprise a valve frame assembly 12, with the valve frame assembly 12 including a lower most annular base ring 14, constructed as seen in top view in FIG. 3, for defining the end flow orifice 16 of the valve stent 10. Annular base ring 14, as seen in FIGS. 1 and 2, is designed, in the case of a heart valve, to substantially match the physiological aortic valve annulus shape corresponding to inflow orifice 6 of valve frame 12. In the case of a vascular valve design, the annular base ring 14 is designed to substantially match the physiological shape of the inner annular wall of the vessel. The base ring 14 includes aperatures 15 for purpose discussed below.

Projecting upwardly from annular ring 14 are three equally spaced apart frame posts 18, 20 and 22, respectively, defining means for supporting the upper valve frame structure of valve stent 10. As illustrated more clearly in cross-sectional views in FIGS. 4 through 6, each of the post members 18, 20 and 22 would include a broadened base portion 19, a vertical post member 21 and an upper portion 23, with the lower most portion 19 of each post injection molded into annular ring 14, and the upper portion 23 of each post 18, 20 and 22, injection molded into the juncture 29 between the scallops of upper ring 25. Holes 19A are inserted in the post member to serve as anchors when the post members are injection molded into the annular ring 14 and the upper ring 25.

For purposes of construction, each of the spring steel portion of each posts 18, 20 and 22 would approximate 0.001 to 0.010 inches in thickness.

Figure 4:
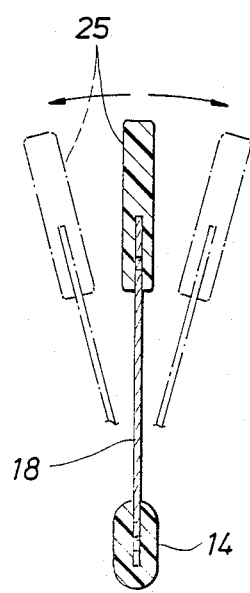
FIG. 4 is a cross-sectional view along line 4—4 in FIG. 3, illustrating a valve stent leg.

With reference to the preferred embodiment, upper scalloped ring 25 would include tri-segmented scalloping rings 26, 28 and 30, each generally defining a paraboloid shaped one-third portion of the base of the valve between the center lines of the respective valve posts, together forming a right cylinder of the inside diameter of valve 10. Therefore, each of the posts 18, 20 and 22 would define a means for supporting the upper ring 25 at the juncture between the three paraboloid-shaped scalloped rings 26, 28 and 30, so that the lower most portion 31 of each of the scalloped rings are supported a distance 27 away from the base ring 14 as seen, for example, in FIG. 1. In addition, as seen in FIG. 4, because the posts are constructed of a flexible steel, when pressures are exerted on the cusps of the valve, the flexible posts 18, 20 and 22 are able to flex, as seen in phantom view in FIG. 4, thus extending the life of the valve.

For purposes of construction, it should be noted that annular ring 14 and upper ring 25, defined by the three paraboloid shaped scalloped rings 26, 28 and 30, are constructed of a spring steel (known under the trademark "ELIGILOY", owned by the Eligiloy to and polymer composite with the spring steel leg members injection molded in place at the base 19 of annular ring 14 and at the upper portion 23 at each juncture 29 of the three scalloped rings 26, 28 and 30. It has been determined that this polymer and spring steel composite structure of the valve stent achieves complete flexibility of the valve stent yet avoids any polymer creep which is a recurring problem in the present state of the art.

In order to further assure that distance 27 is maintained between ring 14 and the lower most portion of each of the scalloping rings, as seen in side views in FIGS. 1 and 2, base ring 14 provides three rises 32 along its length, each rise 32 constituting the point that each leg member 18, 20 and 22 is injection molded into base ring 14. Intermediate each rise 32 there is included a dip 33 in the ring. Each dip 33 corresponds to a point at which the lower most portion 31 of each scalloping ring is situated. Therefore, each dip 33 along the base ring 14 is coincidental with the lower most point 31 of each scalloping ring and assures that distance 27 will be maintained between the base ring 14 and the lower most point 31 of each scalloping ring 26, 28 and 30, so that greater flexibility between base ring 14 and the scalloping rings is maintained.

As is further illustrated in FIGS. 7, 8 and 9, a tricuspid valve body 44 is shown supported by valve stent 10. The body 44 is constructed over stent 10 using state-of-the-art techniques well known to those skilled in the art. Constructed around annular base ring 14 and scalloping rings 26, 28 and 30 is a skirt portion 46 which is sutured onto the heart tissue surrounding the aortic valve annulus in the case of a heart valve or the walls of the vessel in the case of a vascular valve. One end of the skirt portion 46 is attached to the base ring 14 and sutured through aperatures 15. The other end of skirt portion 46 is sutured to the scalloped rings 26, 28 and 30 through aperatures 70. The skirt portion 46 is attached to the scalloped rings to provide a wrapped portion L as shown in FIG. 9 which is the part of skirt portion 46 sutured to the aortic valve annulus or the vessel wall. This maintains the valve securely in position. The wrapped portion L includes a fabric filler 71 to give the portion L body. The fabric filler may be made of any durable yet inert material such as Dacron ® or Teflonp ®. It should be noted that even in spite of securing the valve 10 in position, the design allows free movement of three scalloping rings 26, 28 and 30, therefore providing greater flexibility of the upper valve body during blood flow through the valve.

FIGS. 10 and 11 illustrates the alternate embodiment of the bioprosthetic valve of the present invention. Illustrated therein is a valve sent represented by the numeral 110. The valve stent 110 would comprise a valve frame assembly 112, with the valve frame assembly 112 including a lowermost annular base ring 114. Again, the annular base ring 114 is designed, in the case of the heart valve, to substantially match the physiological aortic valve annulus shape corresponding to the inflow orifice. In the case of a vascular valve design, the annular base ring 114 is designed to substantially match the physiological shape of the inner annular wall of the vessel.

Figure 5:
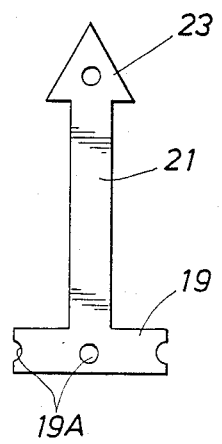
FIGS. 5 and 6 are front and side views respectively of the metallic leg portion of the preferred embodiment of the stent.
Figure 6:
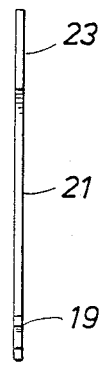

Projecting upwardly from the annular base ring 114 are two equally spaced apart frame posts 118 and 120 which define means for supporting the upper valve frame structure. Each of the post members 118 and 120 would include a broad portion, a vertical member and an upper portion similar to base portion 19, vertical post member 21 and upper portion 23 as shown in FIGS. 4-6 of the preferred embodiment. Again, the upper portion of each post 118 and 120 would be injection molded into the juncture 129 between the scallops of outer ring 125.

The upper scallop ring 125 would include bisegmented scalloped rings 126 and 128, each generally defining a parabolic-shaped one-half portion of the base of the valve between the center lines of the respective valve posts, together forming a right cylinder of the inside diameter of the valve. As discussed above with respect to the preferred embodiment, the construction would be of a polymer and spring steel composite.

Furthermore, as discussed above with respect to the preferred embodiment, the distance 127 between the ring 114 and the lowermost portion 131 of each of the scalloped rings would be maintained by providing the base ring 114 with two rises 132 along its length. As in the preferred embodiment, intermediate each rise 132 there is included a dip 133 wherein each dip 133 corresponds to a point at which the lowermost portion 131 of each scalloped ring is situated. This assures that the distance 127 will be maintained between the dip 133 of base rng 126 and 128.

Other than the structure differences associated with the use of two posts, as opposed to three posts, the construction and performance of the alternate embodiment is identical to that of the preferred embodiment.

The valve stent of the present invention may be utilized to replace a defective aortic valve such as the aortic or mitral valves. Under norml circumstances, the stent would be cloth covered with a tricuspid valve body 44. In the case of the preferred embodiment, three apices of the tri-segmented valve body define the three valve cusps, as are present in the natural aortic valve. Since the aortic and pulmonary valves are similar in configuration as are the mitral and tricuspid valves, and since the valve stent referred to herein as an aortic valve stent is equally suited to the pulmonary valve location, it is to be understood that the terms aortic and mitral are descriptive of the type of application and are not restrictive to a particular anatomical location. For example, as discussed above, the valve may be of a general vascular type for use in a vein or other anatomical vessel. In the case of the alternate embodiment, the stent would be cloth covered with a bicuspid valve body and the two apices of the bi-segmental valve body define the bicuspid valve arrangement. Its use would be similar to that of the preferred embodiment.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A tissue heart valve stent for supporting a valve body and mountable on the tissue surrounding the valve annulus, comprising:
   a. a base ring, consisting essentially of a polymer material, and having an inflow orifice substantially the shape of a heart valve;
   b. an upper tri-segmented parabolic-scalloped ring consisting essentially of a polymer material providing three equally spaced apart valve segments; and
   c. three post members consisting essentially of metallic alloy extending between the annular base ring and supporting and connected to the upper most portion of each of the scalloped rings having elastic properties different from those of either essentially polymeric component so that they allow for relative movement beween the scalloped rings and the annular base ring.

2. The valve stent in claim 1, wherein said valve stent further comprises means for attaching the frame assembly to heart tissue surrounding the valve annulus.

3. The valve stent in claim 1, wherein the parabolic shaped scalloping rings further define a one-third portion of the base between the center line of the post members to form a right cylinder of the inside diameter of the valve.

4. The valve stent in claim 1, wherein the post members are injection molded into the base ring and into the upper ring member.

5. The valve stent in claim 1, wherein there is further provided a tricuspid valve body constructed over the frame for operation of the valve.

6. The valve stent in claim 1, wherein the metallic alloy of the post members further comprises spring steel.

7. The valve stent in claim 1, wherein the post members are injection molded to the upper most portion of each of the scalloped rings.

* * * * *

UNITED STATES PATENT AND TRADEMARK OFFICE
CERTIFICATE OF CORRECTION

PATENT NO. : 4,851,000
DATED : July 25, 1989
INVENTOR(S) : BRIJ M. GUPTA

It is certified that error appears in the above-identified patent and that said Letters Patent is hereby corrected as shown below:

Column 3, line 23, reference number "6" should read -- 16 --.

Column 3, line 68, Eligiloy "to" should read -- Eligiloy Co.) --.

Column 4, line 45, "Teflonp" should read -- Teflon --.

Column 4, line 52, "sent" should read -- stent --.

Column 5, line 23, "rng" should read -- ring 114 and the lowermost point 131 of each scalloped ring --.

Column 5, line 31, "norml" should read -- normal --.

Signed and Sealed this

Twelfth Day of June, 1990

Attest:

HARRY F. MANBECK, JR.

*Attesting Officer*     *Commissioner of Patents and Trademarks*